US00PP10345P

United States Patent [19]

Cosner et al.

[11] Patent Number: Plant 10,345

[45] Date of Patent: Apr. 21, 1998

[54] DOUBLE IMPATIENS PLANT NAMED 'TIOGA WHITE'

[76] Inventors: Harlan B. Cosner; Sue L. Cosner, both of P.O. Box 173, Broadbent, Oreg. 97414

[21] Appl. No.: 694,161

[22] Filed: Aug. 8, 1996

[51] Int. Cl.[6] ..... A01H 5/00

[52] U.S. Cl. ..... Plt./87.6

[58] Field of Search ..... Plt./57.6

*Primary Examiner*—Howard J. Locker

*Assistant Examiner*—Kent L. Bell

[57] ABSTRACT

A distinctive cultivar of Double Impatiens plant named 'Tioga White', characterized by its large pure white flowers; flowers held above the foliage; consistently double and symmetrical flower form; numerous flowers per plant; freely branching plant habit; compact and mounted plant habit; and dark green foliage.

1 Drawing Sheet

The present invention relates to a new and distinct cultivar of Double Impatiens plant, botanically known as *Impatiens walleriana*, and hereinafter referred to by the cultivar name 'Tioga White'.

The new cultivar is a product of a planned breeding program conducted by the inventors in Coquille, Ore. The objective of the breeding program was to develop varieties with attractive flower colors, consistently double flower form, uniform plant habit, and numerous flowers per plant.

The new cultivar originated from a cross made by the inventors of an unnamed proprietary selection as the male or pollen parent with the proprietary selection H-55 as the female or seed parent.

The cultivar 'Tioga White' was discovered and selected by the inventors as a flowering plant within the progeny of the stated cross in a controlled environment in Coquille, Ore. Asexual reproduction of the new cultivar by terminal cuttings taken at Coquille, Ore., has shown that the unique features of this new Double Impatiens are stable and reproduced true to type in successive generations of asexual reproduction.

The following traits have been repeatedly observed and are determined to be the unique characteristics of 'Tioga White'. These characteristics in combination distinguish the new Double Impatiens as a new and distinct cultivar:

1. Large pure white flowers.
2. Flowers held above the foliage.
3. Consistently double and symmetrical flower form.
4. Numerous flowers per plant.
5. Freely branching plant habit.
6. Compact and mounded plant habit.
7. Dark green foliage.

In contrast to plants of the new Double Impatiens, plants of the male parent have blush white semi-double flowers, bronze stems, and a prostrate plant habit; and plants of the female parent have greenish white semi-double flowers.

The new Double Impatiens has not been observed under all possible environmental conditions. The phenotype may vary significantly with variations in environment such as temperature and light level, without, however, any variance in genotype.

The accomanying colored photograph illustrates the overall appearance and flower color of the new Double Impatiens, showing the colors as true as it is reasonably possible to obtain in colored reproductions of this type. The photograph comprises a side perspective view of a typical plant of the new Double Impatiens.

The following observations, measurements, values, and comparisons describe plants grown in Alva, Fla., and Roanoke, Tex.

In the following description, color references are made to The Royal Horticultural Society Colour Chart except where general terms of ordinary dictionary significance are used.

Botanical classification: *Impatiens walleriana* cultivar 'Tioga White'.

Parentage:

*Male or pollen parent.*—Unnamed proprietary selection.

*Female or seed parent.*—Proprietary selection H-55.

Propagation:

*Type cutting.*—Terminal cuttings.

*Time to initiate roots.*—7 to 10 days at 20° C. soil temperature.

*Rooting habit.*—Numerous, fibrous, and well-branched.

Plant description:

*Form.*—Compact, mounded form, uniform, spreading and arching.

*Growth habit.*—Moderately vigorous. Freely branching, dense growth. Suitable for 10 to 25-cm containers.

*Stem.*—Internode length: About 1.5 cm. Color: 144A.

*Foliage description.*—Leaves simple, generally symmetrical, abundant, and flat in aspect. Size, largest leaves: Length: About 5 cm. Width: About 3.5 cm. Shape: Ovate with acuminate tip. Texture: Smooth. Margin: Crenate. Color: Adaxial surface: 147A. Abaxial surface: 139C.

Flower description:

*Flower type and habit.*—Large pure white flowers. Consistently double and symmetrical flowers. Freely and continuously flowering. Flower buds open similar to a rose in fullness. The flowers are borne slightly above the foliage, arising from leaf axils, typically seven flowers per axil, terminal bud opening first. Numerous flowers per plant.

*Time to flower.*—Flowering generally commences four to six weeks after planting.

*Flowering season.*—Year-round under greenhouse conditions. In the garden, flowering is continuous from spring until fall.

*Flower diameter.*—About 3.5 cm.

*Flower depth (height).*—About 2 cm.

*Flower buds.*—Shape: Ovoid. Color: 155D.

*Petals/petaloids.*—Quantity: About 45 per flower. Shape: Round, oblong, or cordate with indentation at tip. Color: Upper side, mature: Iridescent, 155D. Under side, mature: Iridescent, 155D.

*Sepals.*—Quantity: Typically two per flower. Shape: Round with prominent midvein. Color: 143C.

*Spur.*—Shape: Narrow and curved. Quantity: One per flower. Length: About 2.25 cm. Color: 144B.

*Peduncles.*—Length: About 3 cm. Color: 144B.

*Reproductive organs.*—None observed. Under optimal flowering conditions, reproductive organs do not develop.

Disease resistance: Under commercial conditions, resistance nor susceptibility to pathogens has not been observed.

Seed production: Seed production has not been observed.

It is claimed:

1. A new and distinct Double Impatiens plant named 'Tioga White', as illustrated and described.

* * * * *

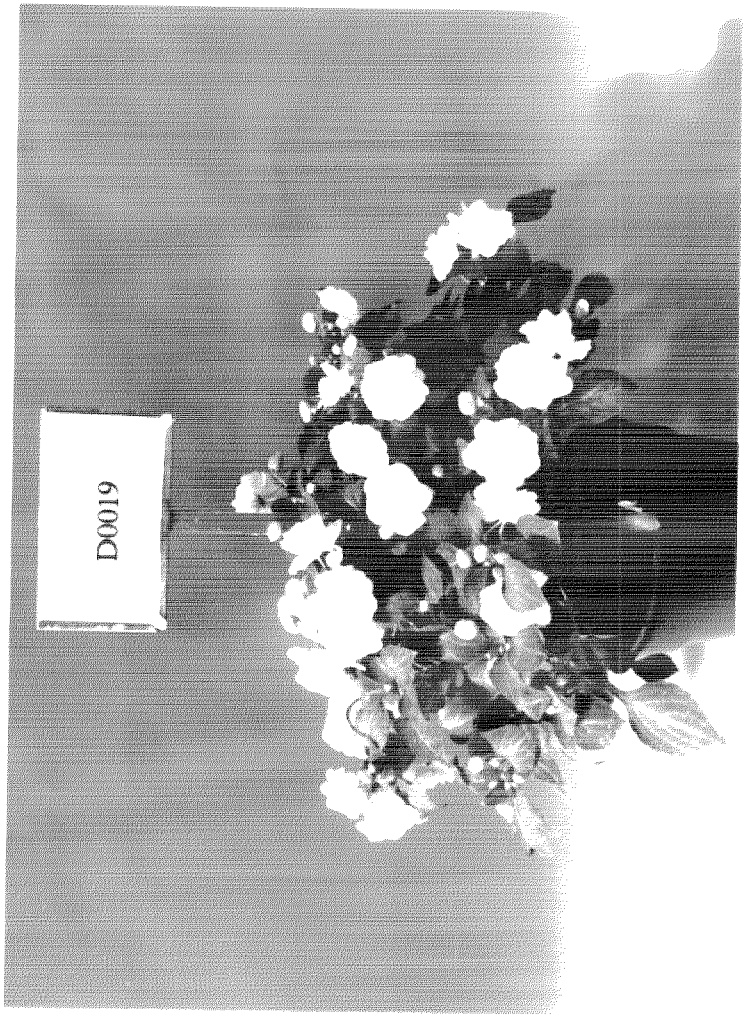
D0019